United States Patent [19]

Sardina

[11] Patent Number: 4,628,136
[45] Date of Patent: Dec. 9, 1986

[54] DEHYDROGENATION PROCESS FOR PRODUCTION OF STYRENE FROM ETHYLBENZENE COMPRISING LOW TEMPERATURE HEAT RECOVERY AND MODIFICATION OF THE ETHYLBENZENE-STEAM FEED THEREWITH

[75] Inventor: Helion H. Sardina, Waldwick, N.J.

[73] Assignee: Lummus Crest, Inc., Bloomfield, N.J.

[21] Appl. No.: 809,913

[22] Filed: Dec. 17, 1985

[51] Int. Cl.$^4$ ............................................. C07C 4/02
[52] U.S. Cl. .................................. 585/441; 585/402; 585/440; 585/914
[58] Field of Search ................ 585/402, 440, 441, 914

[56] References Cited

U.S. PATENT DOCUMENTS

| | | | |
|---|---|---|---|
| 3,256,355 | 6/1966 | Gilman et al. | 585/914 |
| 3,408,263 | 10/1968 | Ward | 585/440 |
| 3,409,689 | 11/1968 | Ward | 585/402 |
| 3,515,764 | 6/1970 | Hallman et al. | 585/402 |
| 3,690,839 | 9/1972 | Jones | 585/402 |
| 3,691,020 | 9/1972 | Hughes | 585/402 |

Primary Examiner—Curtis R. Davis
Attorney, Agent, or Firm—James N. Blauvelt

[57] ABSTRACT

An improved process for the production of styrene through dehydrogenation of ethylbenzene in the presence of steam at elevated temperatures, comprising (1) recovering heat of condensation normally lost during separation of the various components of the dehydrogenation reaction effluent, especially of ethylbenzene from styrene, without need or use of a compressor and (2) using such heat to vaporize an aqueous feed mixture of ethylbenzene and dilution water that is introduced into the dehydrogenation reactor, preferably at about atmospheric pressure, thereby obviating the need to use steam to vaporize the liquid ethylbenzene feed and also enabling much of the diluent steam needed as sensible heat for the dehydrogenation reaction to be generated from water.

11 Claims, 2 Drawing Figures

DEHYDROGENATION PROCESS FOR PRODUCTION OF STYRENE FROM ETHYLBENZENE COMPRISING LOW TEMPERATURE HEAT RECOVERY AND MODIFICATION OF THE ETHYLBENZENE-STEAM FEED THEREWITH

BACKGROUND OF THE INVENTION

1. Field of the Invention

This invention relates to a process for the production of styrene by the dehydrogenation of ethylbenzene in the presence of steam, and more particularly, to a procedure therein for achieving low temperature heat recovery of heat of condensation normally lost during separation of the various dehydrogenation products, most notably of ethylbenzene from styrene, and using such heat to vaporize the liquid ethylbenzene and water feeds to the dehydrogenation reactor without the need or use of a compressor.

2. Description of the Prior Act

It is well known that styrene can be produced from ethylbenzene at temperatures between about 1100 to 1200 degrees F. by vapor phase catalytic dehydrogenation in the presence of steam. Early patents on the subject have concerned themselves essentially with the nature of the catalyst. For example, among the catalysts suggested for this reaction are: palladium oxide catalysts (U.S. Pat. No. 3,502,736); platinum metal catalysts (Japanese Patent Publication No. 8367/67); supported palladium catalysts (Japanese Patent laid-open No. 133236/76); molybdenum-bismuth oxide catalysts (Japanese Patent laid-open No. 52139/76); catalysts containing oxides of at least one metal of copper, zinc, arsenic, antimony, chromium, iron, and/or cobalt (Japanese Patent Publication No. 9168/70); and catalysts containing tin, antimony, and oxygen as essential constituents (British Pat. No. 1,595,008).

More recently, however, the emphasis has shifted from catalyst to means for achieving heat economy in the dehydrogenation process, particularly with regard to the large quantities of diluent steam employed to supply the sensible heat needed for the endothermic reaction in such process and with regard to the separation of styrene from the dehydrogenation reaction effluent products. For example, British Pat. No. 1,122,857 discloses that heat may be transferred from the reactor effluent by using it to generate steam which is thereafter compressed and introduced into the reboiler of the ethylbenzene distillation zone, where styrene is removed by fractionation from ethylbenzene. In this patent, moreover, high pressure steam is used to drive the compressor for the reactor effluent steam generated.

German Offenlegungsschrift No. (OLS) 3,147,323 also focuses on achieving heat economy in the dehydrogenation process. It does so, however, by concentrating on making the dehydrogenation reactor self-sufficient in regard to its steam requirement by recovering the heat, previously abstracted by cooling, for steam generation. Its novelty consists of vaporizing water with a reaction mixture that has been cooled to 90–120 degrees C. and is at a pressure of 0.4–1.2 atm., and compressing the resultant steam to 1.4–2.5 atm. and using it to prepare the ethylbenzene, water, and steam feed mixture. U.S. Pat. No. 3,515,767 embodies the same inventive concept as this Offenlegungsschrift. It teaches the generation of subatmospheric steam from the heat of quenched reaction zone effluent, and compresses the resulting low pressure steam for use, e.g., as reboiler heat in the product recovery fractionation facilities. However, the improvements of these latter two patent publications require, for their inventive success, a compressor, a heavy duty item of equipment involving substantial investment and expense. The present invention has evolved from the need to avoid these problems and to reduce substantially the energy input and plant investment costs associated with the production of styrene through dehydrogenation of ethylbenzene in the presence of steam at elevated temperatures.

To enable use of the vaporized ethylbenzene-steam mixture in the dehydrogenation process without the need of a compressor, the present invention makes use of novel process improvements. For example, the ethylbenzene-water side of the condenser on the fractionating column separating ethylbenzene and styrene is operated at a pressure adequate for flow through the downstream system. Also, by modifying the ethylbenzene-steam feed system through the mixing of liquid ethylbenzene and water feeds and vaporizing same for introduction, at about atmospheric pressure, into the dehydrogenation reactor, it has been found that the need for steam to vaporize the liquid ethylbenzene feed is eliminated and that much of the diluent steam needed as sensible heat for the dehydrogenation reaction can be generated from liquid water. Other process improvements and simplifications are achieved as well.

SUMMARY OF THE INVENTION

The present invention is thus directed to an improved dehydrogenation process for the production of styrene from ethylbenzene, in the presence of steam, at elevated temperatures through recovering heat of condensation normally lost during separation of the various components of the dehydrogenation reaction effluent, especially of ethylbenzene from styrene, without need or use of a compressor, and using such heat to vaporize an aqueous liquid feed mixture of ethylbenzene (EB) and dilution water that is to be introduced into the dehydrogenation feed reactor, preferably at about atmospheric pressure.

BRIEF DESCRIPTION OF THE DRAWINGS

Understanding of the present invention will be facilitated by reference to the following detailed description, taken in light of the accompanying FIGS. 1 and 2.

DETAILED DESCRIPTION OF THE PREFERRED EMBODIMENTS OF THE PRESENT INVENTION

The present dehydrogenation process for the production of styrene comprises dehydrogenation of ethylbenzene, preferably in a multi-bed, preferably two-bed, radial flow reactor, using a conventional catalyst for this purpose, such as one based on iron oxide, and conventional operating conditions.

It is understood that certain equipment such as valves, piping, indicators and controls, and the like have been omitted from the drawings to facilitate the description thereof, and that the placement of such equipment at appropriate places is deemed to be within the scope of one skilled in the art.

Figure 1:
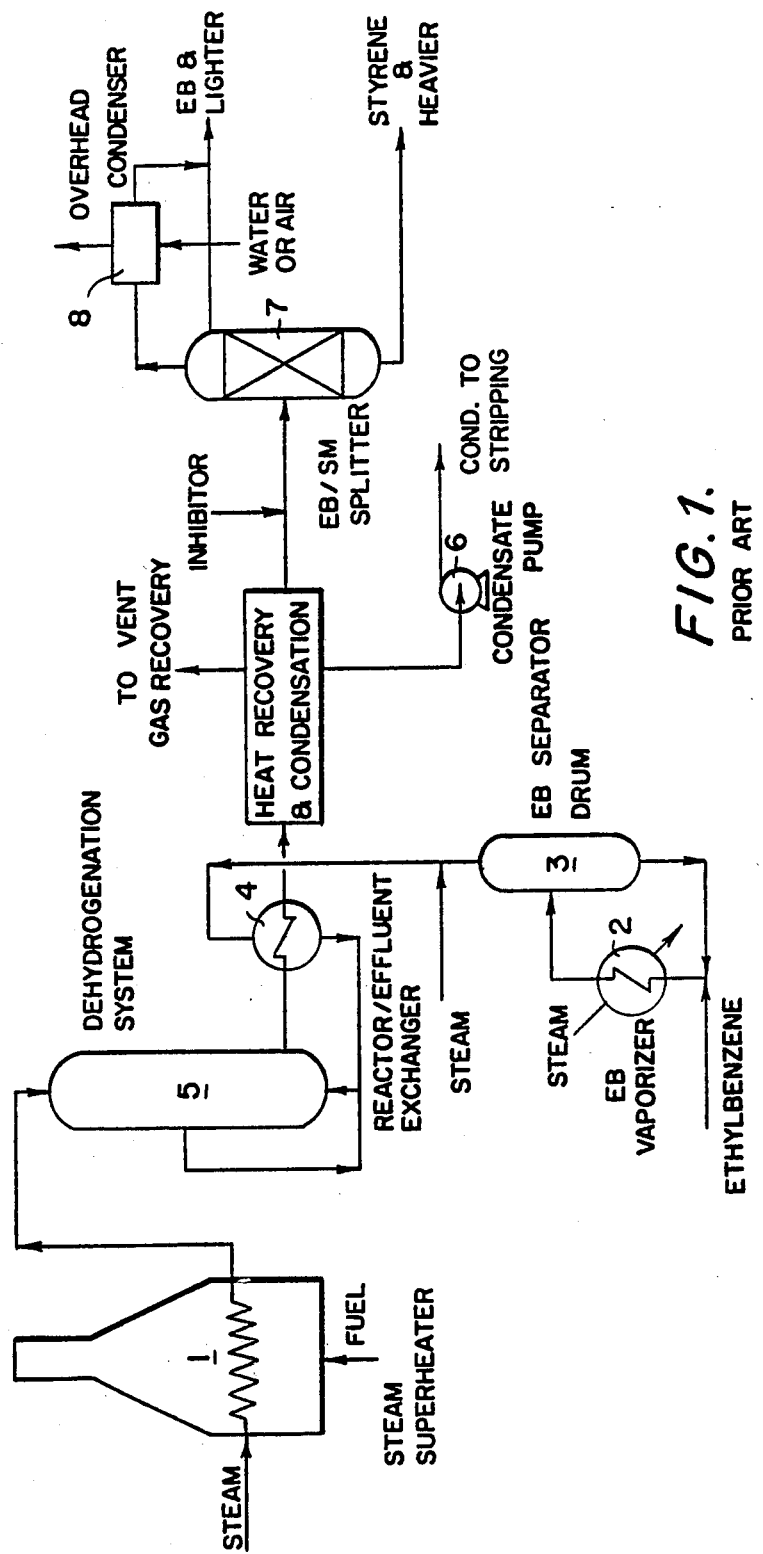
FIG. 1 is a simplified schematic flow diagram of the closest prior art dehydrogenation process for the production of styrene from ethylbenzene, in the presence of steam, at elevated temperatures.

Referring now to FIG. 1, this represents a typical commercial prior art process for the production of styrene through catalytic dehydrogenation of ethylbenzene (EB), at elevated temperatures approximating 600 degrees C. or more and under low pressure, in the presence of dilution steam.

In FIG. 1, there is depicted, schematically, a steam superheater 1, which is a direct fired heater, for superheating a major portion of the diluent steam (main steam) to a temperature above the dehydrogenation reaction temperature.

Feed ethylbenzene is vaporized in an EB vaporizer 2, which is a conventional thermosiphon reboiler, and passed to an EB separator drum 3. From drum 3, the vaporized EB—diluent steam mixture is mixed with a small portion of the diluent steam and superheated by heat exchange in a heat exchanger 4 with the dehydrogenation reaction effluent. It is then further preheated with the superheated main steam with which it mixes at the reactor inlet of the dehydrogenation reactor 5 before reaction in said reactor 5.

The dehydrogenation reaction effluent, after being heat exchanged in exchanger 4, is passed to the heat recovery and condensation section of the process. Such effluent contains primarily styrene, hydrogen, and unreacted ethylbenzene; small or minor amounts of the dealkylation by-products of benzene and toluene; small or minor amounts of methane, ethane, carbon monoxide, carbon dioxide, polymeric materials, and tars; and also an aqueous condensate. The gaseous phase, which includes some of these materials, and comprises hydrogen, methane, ethane, carbon monoxide, carbon dioxide, benzene, and toluene is recovered by means which include compression and aromatics recovery of the benzene and toluene. The aqueous phase, comprising aqueous condensate, is transmitted by a condensate pump 6, subjected to steam stripping, and reused as boiler feed water. The third and final phase, the organic phase, comprises crude styrene, which has to be distilled in order to recover styrene monomer. Conventionally, the crude styrene, together with a polymerization inhibitor, is fed into a distillation tower 7, which is referred to in the art and known as an ethylbenzene-styrene monomer (EB/SM) "splitter". The polymerization inhibitor, as its name suggests, reduces polymer formation during distillation of the crude styrene. EB/SM splitting can comprise a single distillation tower or a plurality of them ("distillation train"). During distillation, the key separation is that between EB and styrene, and column operation is conducted under reduced pressure conditions so as to reduce temperature and thus styrene polymer. Thus, EB and lighter materials are separated from styrene and heavier materials.

Figure 2:
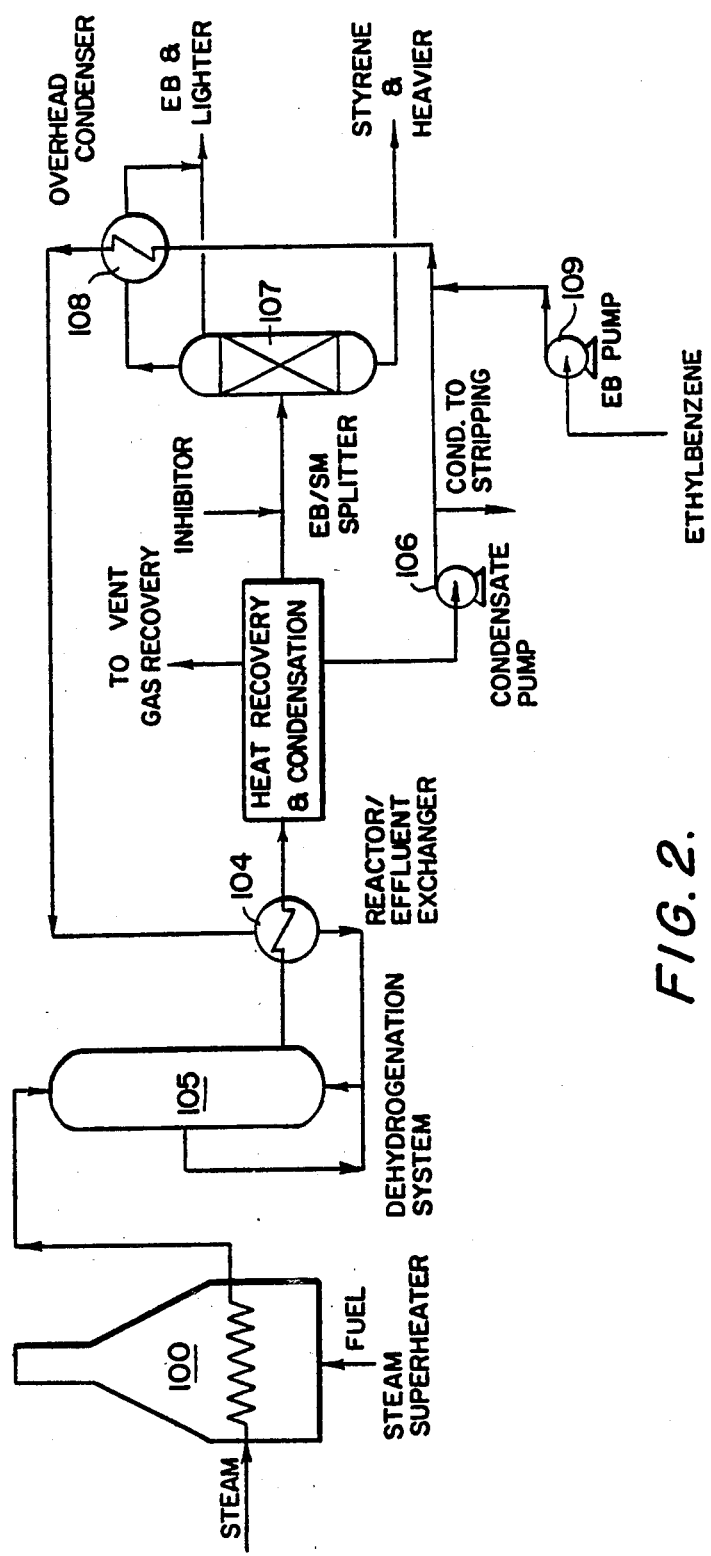
FIG. 2 is a simplified, schematic flow diagram of the present invention, which is an improved version of the prior art process shown in FIG. 1.

Referring now to FIG. 2, shown there is an improved version of the conventional process depicted in FIG. 1. To facilitate comparison of the two figures, the system of numbering of the respective pieces of process equipment in FIG. 2 parallels that adopted for FIG. 1, except for the use of a "100" series rather than a "1" or single-digit series of numbering. In FIG. 2, there is illustrated a dehydrogenation reactor 105 (designated "dehydrogenation system" as in FIG. 1) into which are passed a main supply of steam, preferably superheated steam, transmitted from direct-fired steam superheater 100, and a feed mixture of ethylbenzene and water, preferably process steam condensate, said feed mixture being at about atmospheric pressure. The reaction effluent from dehydrogenation reactor 105 is passed into a heat exchanger 104 which transfers heat from the dehydrogenation reaction effluent to the ethylbenzene-water vapor feed mixture, thereby superheating said feed mixture. From exchanger 104 the superheated gaseous feed mixture is passed to dehydrogenation reactor 105. The cooled dehydrogenation reaction effluent from exchanger 104 is passed into additional heat recovery, condensation, and hydrocarbon/steam condensation units in conventional fashion, as indicated by the block denoted "Heat Recovery & Condensation" in both FIGS. 1 and 2. The uncondensed material that remains after such processing, off-gas, comprising non-condensibles (inerts) and uncondensed hydrocarbons and the remaining steam is compressed, scrubbed, and cooled for additional recovery. These measures are denoted by the expression "vent gas recovery" in FIGS. 1 and 2. The liquid water separated during "heat recovery and condensation" is withdrawn by a condensate pump 106, while the hydrocarbons separated from the aqueous phase during such processing, which hydrocarbons comprise unreacted ethylbenzene, styrene, tars, and by-products of benzene and toluene, are then sent to a fractionation column 107, designated as "EB/SM splitter" to denote its primary function. The overhead from the column 107 comprises unreacted ethylbenzene and the by-products benzene and toluene, which are condensed in the overhead condenser 108 into reflux and overhead product. The bottoms from column 107 comprise styrene and tars, which are withdrawn as a bottoms stream. Fresh feed ethylbenzene from pump 109 is mixed with the required diluent steam condensate from condensate pump 106 to form a minimum boiling mixture of ethylbenzene and water which then circulates through the overhead condenser 108. The required quantity of ethylbenzene-water that is fed to reactor 105 vaporizes while condensing the overhead vapor from overhead condenser 108. The net weight ratio of water to ethylbenzene may vary from 0.3 to 0.6, with the preferred ratio being 0.40 to 0.50. The origin of the supply of water is not a critrcal factor and may be drawn from a variety of sources available in the plant. Most common sources of water would derive from various steam condensates such as process steam condensate or stripped process condensate.

In one of its major, essential aspects, there is provided in this invention an improved method for producing the ethylbenzene-steam feed vapor mixture, thereby conserving considerable amounts of energy and plant investment capital. This method can be employed in all standard conventional commercial styrene processes based upon the dehydrogenation of ethylbenzene in the presence of steam, and it conserves energy whether employed in an adiabatic or an isothermal dehydrogenation process.

To enable use of the vaporized ethylbenzene-steam mixture in the dehydrogenation process without the need for a compressor, the ethylbenzene steam side of the overhead condenser 108 on the fractionating column 107 is operated at a pressure adequate for flow through the downstream system. While not wishing to be limited to specific numerical values, which are variable and dependent on a number of other process factors as is known in the art, nevertheless, for purposes of illustrating this invention, such ethylbenzene steam side pressures of condenser 108 would approximate about 8 to about 25 psi absolute. And the column overhead pressures would approximate about 100 to about 1300 mm mercury, preferably about 100 to 400 mm.

Thus the operating pressure of column 107 is thereby increased from below about 100 mm mercury to give a temperature differential between the condensing ethylbenzene vapor and the vaporizing ethylbenzene-water feed mixture. This differential can be enhanced by the use of a polymerization inhibitor that permits raising of the EB/SM splitter column 107 operating pressure, and thus temperature, without a significant increase in the quantity of styrene polymer produced. Any styrene polymerization inhibitor that meets these requirements would be utilizable in this invention. Thus, examples of suitable polymerization inhibitor would include both sulfur compounds such as sulfur or, more preferably, non-sulfur compounds such as various types of organic compounds, preferably aromatic nitrogen-containing compounds and most preferably aromatic nitro compounds. Representative examples of preferred organic compounds include the following: bis-(2,2,6,6)-tetramethyl piperidyl-1-hydroxylamide adipate; various mixtures of dinitroethyl phenol and dinitrochlorophenol such as 2,6-dinitro-4-ethylphenol and 2,6-dinitro-4-chlorophenol (see U.S. Pat. No. 4,474,646); various mixtures of para-nitrophenol, Mannich base, and paraquinone dioxime (see U.S.S.R. Pat. No. 968,041); tetra 3,5 ditertiary-butyl-4-hydroxybenzyl ethylenediamine; dinitro-phenylhydrazine or diphenyl-carbo hydrazide; 4-nitroanthraquinone; 2-methylbenzoquinone-4-oxime; 2,3,5-trimethylbenzoquinone-4-oxime; various mixtures of quinone alkide and a phenol (see U.S. Pat. No. 4,040,911); dinitrophenol (see U.S. Pat. Nos. 3,959,395 and 4,033,829); nitrocresol (see U.S. Pat. No. 4,086,147); phenothiazine; t-butyl catechol; nitrosodiphenylamine; and nitrosomethylaniline (see U.S. Pat. No. 4,050,943).

The steam produced in the vaporization of the ethylbenzene-water feed mixture forms part of the diluent steam. Thus, the relative quantity of dilution steam passing through the steam superheater can be reduced with a consequent reduction in the fuel requirements of the superheater. This additional heat input to achieve the same reactor inlet temperature and dilution steam rate is most conveniently taken from the heat recovery system. Thus, the heat normally lost to the operating environment from the distillation column condenser is used to produce steam and ethylbenzene vapor. And hence net steam import is reduced correspondingly. For any given dehydrogenation reactor configuration and operating conditions, plant investment is also reduced since the steam superheater and the distillation column or system become smaller and hence less expensive. In addition, as previously noted, no compressor is needed.

As can be seen, the present invention is not limited to any specific set of process operating conditions or to any specific equipment arrangement. Total dilution steam-ethylbenzene feed ratios, ethylbenzene conversions, dehydrogenation catalyst identities and compositions, and dehydrogenation reactor system configurations can be varied within sundry operable limits without affecting the nature or scope of this invention. Similarly, process details relative to heat recovery and condensation, vent gas recovery, condensate stripping, and the arrangement of the crude styrene distillation column, i.e. EB-SM splitter, are not critical to the success of this invention. Likewise, whether benzene and toluene are separated before or after ethylbenzene and styrene are separated is also a matter not critical to the practice of this invention.

Moreover, this invention offers the same attractive advantages over other methods of producing superheated ethylbenzene or superheated ethylbenzene-steam dehydrogenation reactor feed. For example, ethylbenzene can be vaporized by heat exchange with dehydrogenation reactor effluent, and superheating of the ethylbenzene-steam vapor can be accomplished in the convection section of the steam superheater.

The following table summarizes the typical operating ranges in important dehydrogenation process parameters for styrene processes in which the present invention can be implemented, whether under adiabatic or isothermal conditions.

|  | Adiabatic | Isothermal |
| --- | --- | --- |
| Steam/EB Ratio, wt | 1.0–2.2 | 0.5–1.5 |
| EB Conversion, % | 50–90 | 50–90 |
| Dehydrogenation Temperature, deg. C. | 530–650 | 530–720 |
| Dehydrogenation Pressure, kg/cm$^2$A | 0.3–1.5 | 0.3–1.5 |

EXAMPLES OF THE INVENTION

The invention will now be further illustrated by reference to the following specific, non-limiting, comparative example in which two process schemes are compared for a conventional 60,000 metric tons per year styrene plant using benzene and ethylene feedstocks. In one scheme, Scheme A, the present method disclosed and claimed for producing the ethylbenzene-steam vapor feed mixture was absent. In the second scheme, Scheme B, the present method disclosed on page 6, line 24 to page 10, line 19, for producing the ethylbenzene-steam vapor feed mixture was included. The dehydrogenation reaction systems for both schemes were the same, and the recovered vent gas was used as a fuel for the steam superheater. The figures given below for Schemes A and B are based upon 1.0 kilogram of styrene product. All other factors remained constant.

|  | Scheme A | Scheme B |
| --- | --- | --- |
| Steam import, kg | 1.729 | 0.995 |
| Fuel import, kcal | 726 | 614 |
| Cooling water (10 deg. C. min.) kg | 113 | 65 |
| Loss to polymer, kg | 0.001 | 0.0025 |

The above comparison shows that, in Scheme B, where the present invention was incorporated into the scheme of Process Scheme A, the plant investment cost of Process Scheme A was reduced by 2–3%. It is to be understood, of course, that such savings will vary, depending upon the dehydrogenation system used and upon the economic factors affecting design optimization such as feedstock and utility costs. It is to be further understood that the loss to polymer could be reduced by increasing the rate or amount of feed of the polymerization inhibitor, consistent with the operating limits of the other styrene process parameters.

While the present invention has been described and illustrated with exemplary embodiments, it will be understood that many modifications thereof will be apparent to those of ordinary skill in the art and that this invention is intended to cover such modifications or any adaptations or variations thereof.

What is claimed is:

1. In a process for the production of styrene from the catalytic dehydrogenation of ethylbenzene in a dehydrogenation zone at elevated temperatures in the presence of steam, whereby the dehydrogenation effluent is cooled and then separated into three phases consisting of a gaseous phase comprising hydrocarbons, an aqueous phase comprising steam condensate, and an organic phase comprising crude styrene and unreacted ethylbenzene, and whereby said crude styrene is separated from said unreacted ethylbenzene by distillation and the styrene monomer product is recovered, the overhead from the distillation column for separating said crude styrene from said unreacted ethylbenzene being passed into a condenser in indirect heat exchange with a fluid comprising ethylbenzene and water passing through said condenser, the improvement comprising operating the ethylbenzene—water side of said condenser at a pressure between about 8 psia and about 25 psia; operating said column under conditions sufficient for its overhead to have a pressure in excess of about 100 mm mercury; said fluid comprising water and ethylbenzene and being vaporized during said indirect heat exchange into a gaseous mixture; and said gaseous mixture being passed into said dehydrogenation zone.

2. A process for the production of styrene according to claim 1, wherein the net weight ratio of water to ethylbenzene in said gaseous mixture is from about 0.3 to about 0.6.

3. A process for the production of styrene according to claim 2, wherein said net weight ratio is about 0.4 to about 0.5.

4. A process for the production of styrene according to claim 2, wherein the pressure of said overhead is above about 100 mm mercury to about 1300 mm mercury.

5. A process for the production of styrene according to claim 1 or 4, wherein the water in said gaseous mixture is derived from steam condensate.

6. A process for the production of styrene according to claim 1, 2, or 4, further comprising a polymerization inhibitor being present during the separation of crude styrene from unreacted ethylbenzene in said column.

7. A process for the production of styrene according to claim 1, wherein the diluent steam/ethylbenzene weight ratio is between 1.0–2.2, the ethylbenzene conversion rate is 50–90%, the temperature in the dehydrogenation zone ranges from 530–650 degrees C., and the pressure in the dehydrogenation zone ranges from 0.3–1.5 kg/cm$^2$A.

8. A process for the production of styrene according to claim 1, wherein the diluent steam/ethylbenzene weight ratio is between 0.5–1.5, the ethylbenzene conversion rate is 50–90%, the temperature in the dehydrogenation zone ranges from 530–720 degrees C., and the pressure in the dehydrogenation zone ranges from 0.3–1.5 kg/cm$^2$A.

9. A process for the production of styrene according to claim 1, wherein the temperature differential between the condensing ethylbenzene vapor in said condenser and the vaporizing ethylbenzene-water gaseous mixture in said condenser is between about 2 degrees C. and about 10 degrees C.

10. A process for the production of styrene according to claim 6, wherein said polymerization inhibitor is an aromatic nitro compound.

11. In a process for the production of styrene from the catalytic dehydrogenation of ethylbenzene in a dehydrogenation zone at elevated temperatures in the presence of steam, whereby the dehydrogenation effluent is cooled and then separated into three phases consisting of a gaseous phase comprising hydrocarbons, an aqueous phase comprising steam condensate, and an organic phase comprising crude styrene and unreacted ethylbenzene, and whereby said crude styrene is separated from said unreacted ethylbenzene by distillation and the styrene monomer product is recovered, the overhead from the distillation column for separating said crude styrene from said unreacted ethylbenzene being passed into a condenser into indirect heat exchange with a fluid passing through said condenser, the improvement comprising operating the ethylbenzene steam side of said condenser at a pressure between about 8 psia and about 25 psia; operating said column under conditions sufficient for its overhead to have a pressure in excess of about 100 mm mercury-about 1300 mm mercury; said fluid comprising water and ethylbenzene and being vaporized during said indirect heat exchange into a gaseous mixture; said gaseous mixture being passed into said dehydrogenation zone; the net weight ratio of water to ethylbenzene in said gaseous mixture being from about 0.3-about 0.6; and a polymerization inhibitor being present during the separation of crude styrene from unreacted ethylbenzene in said column.

* * * * *